United States Patent [19]

Re et al.

[11] 4,054,608

[45] Oct. 18, 1977

[54] METHOD FOR THE PREPARATION OF 4-CHLORO-2-METHYL-CROTONALDEHYDE

[75] Inventors: Luciano Re; Giancarlo Eletti Bianchi; Felice Centini, all of Rome, Italy

[73] Assignee: Anic S.p.A., Italy

[21] Appl. No.: 685,317

[22] Filed: May 11, 1976

[30] Foreign Application Priority Data

May 12, 1975 Italy .................................. 23199/75

[51] Int. Cl.$^2$ ............................................. C07C 47/14
[52] U.S. Cl. ................................................ 260/601 H
[58] Field of Search ................................... 260/601 H

[56] References Cited

U.S. PATENT DOCUMENTS

3,268,430  8/1966  Brois et al. .................. 260/601 H

Primary Examiner—James O. Thomas, Jr.
Assistant Examiner—W. B. Lone
Attorney, Agent, or Firm—Morgan, Finnegan, Pine, Foley & Lee

[57] ABSTRACT

In the preparation of 4-chloro-2-methyl-crotonaldehyde, an important starting material for the preparation of the acetate of Vitamin A, the improvement consisting in that isoprene monoepoxide (1:2-epoxy-2-methyl-3-butene) is chlorinated either with tert.butyl hypochlorite in the vapor phase, or with cupric chloride in the liquid phase. The reaction is preferably carried out in an inert siliceous or aluminous substrate at temperatures ranging from 60° C to 150° C. Lithium chloride has proven to be useful as a catalyst, but by no means essential.

7 Claims, No Drawings

METHOD FOR THE PREPARATION OF 4-CHLORO-2-METHYL-CROTONALDEHYDE

This invention relates to a method for the preparation of 4-chloro-2-methyl crotonaldehyde starting from 1:2-epoxy-2-methyl-3-butene (isoprene monoepoxide) which is subjected to appropriate chlorination reactions.

Among the halogenated derivatives of 2-methyl-crotonaldehyde, the importance of the 4-chloro derivative is known, as it is utilized as a starting compound for the synthesis of 4-acetoxy-2-methyl crotonaldehyde, which, in its turn, is an important intermediate in one of the industrial syntheses of Vitamin A acetate.

A simple and economical way has now been found for preparing the 4-chloro-derivative of 2-methyl crotonaldehyde, and, by analogy, the other halogenated derivatives, which is based on simple chlorination (halogenation) reactions of isoprene monoepoxide, which, in its turn, can easily be obtained with conventional methods and, in a still more advantageous way, according to what has been disclosed in a copending application in the name of the same applicants hereof.

Reference will be had, in the progress of this specification and to afford a beter understanding of the invention, to the chlorination reaction of isoprene monoepoxide inasmuch as the other halogenated derivatives can be obtained by mere variations of the same method, which are within the purview of those skilled in the art and can be carried out without departing from the scope of the present invention.

According to the present invention, isoprene monoepoxide can be chlorinated to give 4-chloro-2-methyl crotonaldehyde either with tert.butyl hypochlorite in the vapor phase on an appropriate substrate, or with cupric chloride in the liquid phase.

In both cases there is also formed, in addition to that crotonaldehyde, tiglic aldehyde (2-methyl crotonaldehyde) by rearrangement of the isoprene monoepoxide.

The latter aldehyde, which is formed in variable amounts according to the reaction conditions, can be separated by distillation of the final reaction mixture and, in its turn, chlorinated with cupric chloride, according to a method disclosed by H.K.Dietl et al, Tetrahedron Lett., 1719 (1973), to give additional quantities of 4-chloro-2-methyl-crotonaldehyde.

Tiglic aldehyde chlorination tests, both with tert.butyl hypochlorite and with cupric chloride under the reaction conditions used for isoprene monoepoxide caused virtually no formation of 4-chloro-2-methyl crotonaldehyde.

This is an evidence of the fact that, thus, tiglic aldehyde is not an intermediate in the formation of the chloroaldehyde of the isoprene monoepoxide in the above indicated reactions, but, only, a reaction product concurrent with the chlorination of isoprene monoepoxide itself, which, however, does not prejudice the obtainment of high yields of 4-chloro-2-methyl-crotonaldehyde since tiglic aldehyde can easily be converted into the desired product.

More exactly, the chlorination in the vapor phase of isoprene monoepoxide with tert.butyl hypochlorite (preferably in an equimolecular ratio relative to the epoxide) is carried out at a temperature ranging from 60° C to 150° C (preferably in the vicinity of 125° C) on a substrate composed of silica and/or alumina (preferably alumina alone) and under a stream of an inert carrier gas (such as nitrogen).

The above recalled reaction can be effected either in the presence or in the absence of an inert solvent, such as polychlorinated hydrocarbons, such as carbon-4-tetrachloride.

Chlorination in the liquid phase of isoprene monoepoxide with cupric chloride in at least stoichiometric amounts (2 mols per mol of epoxide) is carried out at a temperature ranging between 20° C and 150° C, in a solvent which can be selected from a wide range of solvents such as, for example, water, dioxane, tetrahydrofuran, acetic acid and its esters, or chloroform or their mixtures and at a pressure which permits the desired temperature to be attained for the reaction; for this reaction it is preferred, however, to operate in a chloroform-ethyl acetate mixture at the refluxing temperature under atmospheric pressures (75° C).

For the above indicated chlorination with cupric chloride, the addition of lithium chloride (preferably in an equimolecular ratio with respect to the epoxide) accelerates the reaction but is not imperative. Lithium chloride can be recovered, at any rate, on completion of the reaction since it merely acts as a catalyst.

It is to be borne in mind, moreover, that in the above indicated chlorination reactions with tert.butyl hypochlorite and cupric chloride, these reactants can economically be regenerated, as is known to anyone skilled in the art, from the respective reaction products: tert-.butyl hypochlorite from tert.butyl alcohol, for example, with molecular chlorine and sodium hydroxide, and cupric chloride from cuprous chloride, for example with air and aqueous hydrogen chloride.

Also in the chlorination of the epoxide with cupric chloride, if the reaction is carried out in an oxygen atmosphere (or in air) in the presence of hydrochloric acid in an amount which is at least equimolecular relative to the epoxide, and of water, the cupric chloride can be used in catalytic amounts, since in such a system the cuprous chloride is oxidized again to cupric chloride as soon as it is formed.

EXAMPLE 1

Preparation of 4-chloro-2-methyl crotonaldehyde from isoprene monoepoxide with cupric chloride in stoichiometric amounts, in the presence of lithium chloride A solution of 20.2 grams (240 millimols) of isoprene monoepoxide in 240 mls of chloroform is supplemented by 240 mls of ethyl acetate, 81.6 grams (480 millimols) of bihydrated cupric chloride and 10.01 grams (240 millimols) of lithium chloride.

The mixture is refluxed (bath temperature 90° C) during 30 minutes and then poured on 240 grams of ice, the formed cuprous chloride being filtered off.

The organic phase is separated from the aqueous phase and the latter is extracted with 240 mls of hexane. The organic phases, combined, are washed to neutrally with water, dried over anhydrous sodium sulfate and distilled at room temperature under a vacuum of 10–20 millimeters of mercury to remove the solvents.

During this stage also a portion of the as-formed tiglic aldehyde is distilled, as a reaction by-product. It can be isolated from the distillate by fractional distillation of the latter under atmospherical pressures, tiglic aldehyde distilling at 117° C–118° C. From the residue of the above indicated distillation at 10–20 millimeters of mercury, by additional distillation in vacuo (120 mms Hg), the remaining tiglic aldehyde is recovered (b.p. 63° C-65° C). All the thusly recovered tiglic aldehyde amounts to 4 grams, equal to a yield of 20% relative to the charged-in epoxide. The residue of the last distillation (at 120 mms Hg), 29 grams, is 4-chloro-2-methyl crotonaldehyde having a gaschromatographic purity of 78% (steel column, length 1.8 meters, ⅛ inches diameter) stationary phase; methylsilicone polymer SE 30, 4% on silanized Chromosorb G, 60-80 mesh; carrier gas:helium, at 0.25 liters per second; column temperature: 80° C-180° C (10° C per minute); internal standard -nor.dodecane, that which corresponds to a yield of 80% (relative to the charged-in epoxide) of pure chloroaldehyde.

The thusly obtained 78% chloroaldehyde can directly be used for the preparation of 4-acetoxy-2-methyl crotonaldehyde.

Should it be desired, conversely, further to purify the aldehyde, it can be distilled once more in a vacuum of 0.5 millimeters of mercury, b.p. 41° C-43° C.

EXAMPLE 2

Preparation of 4-chloro-2-methyl crotonaldehydde from isoprene monoepoxide with stoichiometric cupric chloride, without lithium chloride The procedure is the same as in Example 1 but without adding lithium chloride, but the reaction times are longer: 2.5 hours.

There are obtained 28 grams of 4-chloro-2-methyl crotonaldehyde having a purity of 75%, corresponding to a yield of 75% of pure chloroaldehyde, and 2.6 grams of tiglic aldehyde, corresponding to a yield of 13%.

EXAMPLE 3

Preparation of 4-chloro-2-methyl crotonaldehyde from isoprene monoepoxide with catalytic cupric chloride, in the presence of lithium chloride A 4-necked, 500 ml flask equipped with paddle stirrer, bubble condenser and two charging funnels which contain, respectively, 3.2 mls of 37% aqueous hydrogen chloride (33 millimols) and a solution of 2.52 grams (30 millimols) of isoprene monoepoxide in 30 mls of chloroform, is charged with 30 mls of ethyl acetate, 30 mls of water, 1 gram (5.8 millimols) of bihydrated cupric chloride, and 1.26 grams (30 millimols) of lithium chloride.

In the reaction flask, an oxygen atmosphere is provided and is isolated from the outside by means of a mercury trap. A 95° C bath is then applied and, as soon as the reflux of the mixture contained in the flask, there are added through the charging funnels simultaneously, dropwise and with a vigorous stirring, the solution of isoprene monoepoxide in chloroform and the hydrochloric acid. The speed of the addition of the two solutions is adjusted in such a way that these additions are completed, for both the solutions, after 1 hour approximately.

To the reaction mixture there are added now 50 grams of ice, the organic phase is separated from the aqueous one and the latter is extracted with 200 mls of hexane. The combined organic phases are washed to neutrality with water and dried over anhydrous sodium sulfate. Gaschromatographic tests of the solution indicate a yield of formation of 4-chloro-2-methyl crotonaldehyde of 23% (for the conditions of the gaschromatigraphic test see example 1) and of tiglic aldehyde of 36% (gaschromatographic conditions: column and filler as in example 1; carrier gas: helium at 0.25 mls per second; column temperature: 80° C isothermally during 1 minute, then 80° C-180° C at 30° C per minute; internal standard: nor.tetradecane) which can be isolated by distillation as disclosed in example 1.

EXAMPLE 4

Preparation of 4-chloro-2-methyl crotonaldehyde from isoprene monoepoxide with tert.butyl hypochlorite The reaction is caused to take place in the vapor phase using the following implementation: a glass column, placed in the vertical position, having an inside diameter of 10 millimeters and a length of 30 centimeters, equipped with an outer jacket with circulation of glycerol heated to 125° C, is filled on the bottom and along a height of 20 centimeters with ⅛inches alumina pellets.

To the top opening of the column there is applied a charging funnel with pressure compensator and an outer jacket filled with acetone and dry ice (temp. from −20° C to −30° C) and to the bottom opening a large test tube is applied, immersed in liquefied air and equipped with a lateral tube filled with calcium chloride.

Air is removed from the apparatus by a nitrogen stream and the funnel is charged with 13.0 grams (155 millimols) of isoprene monoepoxide, followed, after a few minutes (as the epoxide has been cooled) by 16.8 grams (155 millimols) of tert.butyl hypochlorite. Dripping of this mixture on the pellet mass is carried out at the speed of one drop every 4 seconds and by applying to the charging funnel a nitrogen stream of 6 liters an hour.

Gaschromatrographic tests on the collected product (24 grams) indicate a yield of formation of 4-chloro-2-methyl crotonaldehyde of 37% (for the gaschromatographic conditions see example 1) and an equal yield of formation of tiglic aldehyde (for the gaschromatographic conditions see example 3).

These products can be isolated by fractional distillation: tiglic aldehyde is distilled at 63° C-65° C at 120 millimeters of mercury and the chloraldehyde at 41° C-43° C at 0.5 millimeters of mercury.

EXAMPLE 5

Preparation of 4-chloro-2-methylcrotanoldehyde from isoprene monoepoxide with tert.butyl hypochlorite in solution in carbon tetrachloride The procedure is the same as in example 4, starting however from a solution of 12.6 grams (150 millimols) of isoprene monoepoxide in 240 mls of $CCl_4$ and adding thereto 16.3 grams (150 millimols) of tert-butyl hypochlorite.

Gaschromatographic tests indicate a yield of formation of 4-chloro-2-methyl crotonaldehyde of 29% and of tiglic aldehyde of 41%.

What we claim is:

1. The method of preparing 4-chloro-2-methyl- crotonaldehyde, which comprises subjecting 1: 2-epoxy-2-methyl-3-butene to chlorination reaction with a chlorinating agent consisting of cupric chloride in the liquid phase or tert-butyl hypochlorite in the vapor phase on a substrate selected from the group consisting of silica and alumina and combinations thereof.

2. A method as claimed in claim 1, wherein said chlorinating agent is tert butyl hypochlorite and the reaction takes place at temperatures ranging from 60° C to 150° C.

3. A method as claimed in claim 2, wherein the reaction is carried out in an inert gas atmosphere.

4. A method as claimed in claim 2, wherein the reaction is carried out in the presence of a solvent selected from the group consisting of the polychlorinated hydrocarbons.

5. A method as claimed in claim 1, wherein said chlorinating agent is cupric chloride and the reaction takes place at temperatures ranging from 20° C to 150° C.

6. A method as claimed in claim 5, wherein the reaction is carried out in the presence of a solvent selected from the group consisting of water, dioxane, tetrahydrofuran, acetic acid and esters threof, chloroform, and mixture thereof.

7. A method as claimed in claim 5, wherein the reaction is carried out in the presence of lithium chloride.

* * * * *